US007618656B2

(12) United States Patent
Hallenbeck et al.

(10) Patent No.: US 7,618,656 B2
(45) Date of Patent: *Nov. 17, 2009

(54) METHOD FOR USE OF LANTHANUM CARBONATE PHARMACEUTICAL COMPOSITIONS

(75) Inventors: Donald Hallenbeck, West Lafayette, IN (US); Simon Bates, West Lafayette, IN (US)

(73) Assignee: Shire International Licensing B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/932,367

(22) Filed: Oct. 31, 2007

(65) Prior Publication Data

US 2008/0089948 A1    Apr. 17, 2008

Related U.S. Application Data

(63) Continuation of application No. 11/418,666, filed on May 5, 2006.

(51) Int. Cl.
*A61K 33/00* (2006.01)
*A61K 31/28* (2006.01)
*A01N 59/00* (2006.01)
*A01N 55/02* (2006.01)

(52) U.S. Cl. ................................ 424/715; 514/492

(58) Field of Classification Search ............ None
See application file for complete search history.

(56) References Cited

U.S. PATENT DOCUMENTS

| | | | |
|---|---|---|---|
| 4,246,246 A | 1/1981 | Nakamura et al. |
| 5,045,289 A | 9/1991 | Fernando et al. |
| 5,503,815 A | 4/1996 | Ishii et al. |
| 5,562,921 A | 10/1996 | Sherman et al. |
| 5,853,758 A | 12/1998 | Lo |
| 5,968,976 A | 10/1999 | Murrer et al. |
| 6,055,293 A | 4/2000 | Secrest |
| 6,160,016 A | 12/2000 | DeLuca |
| 6,281,503 B1 | 8/2001 | Lazarev et al. |
| 6,678,347 B1 | 1/2004 | Kozaczek et al. |
| 6,790,343 B2 | 9/2004 | Wang et al. |
| 7,078,059 B2 | 7/2006 | Atherton et al. |
| 7,184,517 B2 | 2/2007 | Kern et al. |
| 7,256,049 B2 | 8/2007 | Bennett et al. |
| 2001/0014352 A1 | 8/2001 | Batra et al. |
| 2003/0121824 A1 | 7/2003 | Wang et al. |
| 2003/0198997 A1 | 10/2003 | Von Dreele |
| 2004/0161474 A1 | 8/2004 | Moerck et al. |
| 2005/0054077 A1 | 3/2005 | Bennett et al. |
| 2006/0002837 A1 | 1/2006 | Moerck et al. |
| 2006/0083791 A1 | 4/2006 | Moerck et al. |
| 2006/0121127 A1 | 6/2006 | Ferdinando et al. |
| 2006/0134225 A1 | 6/2006 | Moerck et al. |
| 2006/0153932 A1 | 7/2006 | Ferdinando et al. |

FOREIGN PATENT DOCUMENTS

| | | |
|---|---|---|
| JP | 62145024 | 6/1987 |
| WO | WO-9630029 | 10/1996 |
| WO | WO 00/79252 | 12/2000 |
| WO | WO-03053432 | 7/2003 |

OTHER PUBLICATIONS

Barnett, Stephanie, "X-Ray Powder Diffraction Studies of Ettringite and Related Systems," Staffordshire University, 6 pages, http://web.archive.org/web/20040611022250/http://www.geocities.com/j_bunford/ (accessed Aug. 3, 2007).
Litteer, Brian et al., "Increasing Application of X-Ray Powder Diffraction in the Pharmaceutical Industry," American Laboratory, Jun. 2005, 37(12):22-23.
"Lanthanum Carbonate," MDXexchange, Dec. 2004, 7 pages, http://www.micromedex.com/products/updates/drugdex_updates/de/lanthanum.html (accessed Aug. 3, 2007).
Aldrich Handbook of Fine Chemicals and Laboratory Equipment, 2000-2001, p. 1001, www.sigma-aldrich.com.
International Search Report and Written Opinion mailed Feb. 15, 2008, which issued during the prosecution of International Patent Application No. PCT/US 07/61461 (7 pages).
European Patent Office Action dated Feb. 20, 2008, which issued during the prosecution of European Patent Application No. 06 252 404.6, and which corresponds to the present application (4 pages).
Ansel, Howard et al., "Pharmaceutical Dosage Forms and Drug Delivery Systems," 7th Ed., Lippincott Williams & Williams, Philadelphia, pp. 217-218, 1999.
"FDA Approves Fosrenol (R) to Reduce Phosphorous Levels in End-Stage Renal Disease Patients," RedOrbit News, Oct. 27, 2004, 11 pages http://www.redorbit.com/modules/news/tools.php?tool=print&id=98076 (accessed Feb. 5, 2009).
Hutchison, Alastair J. et al., "Long-Term Efficacy and Safety Profile of Lanthanum Carbonate: Results for up to 6 Years of Treatment," Nephron Clinical Practice 110, pp. c15-c23, 2008.
"ICH Harmonised Tripartite Guideline: Impurities in New Drug Products Q3B(R2)," International Conference on Harmonisation of Technical Requirements for Registration of Pharmaceuticals for Human Use, Step 4 Version, Jun. 2, 2006, 15 pages http//www.ich.org/cache/compo/276-254-1.html.
Jonasson, R. G. et al., "Solubilities of some hydrous REE phosphates with implications for diagenesis and sea water concentrations," Geochimica et Cosmochimica Acta, vol. 49, pp. 2133-2139, Jul. 12, 1985.
Letter (Redacted) from Barr Laboratories, Inc. to Shire Biochem Inc., "Notice of ANDA . . . Concerning Lanthanum Carbonate . . . With Paragraph IV Certification Concerning U.S. Patent Nos. 5,968,976, 7,381,428, and 7,465,465," Feb. 2, 2009, 75 pages.

(Continued)

*Primary Examiner*—Ernst V Arnold
(74) *Attorney, Agent, or Firm*—Darby & Darby P.C.; Lydia G. Olson

(57) ABSTRACT

A method for treating hyperphosphatemia using lanthanum carbonate, including analytically determining the amount of an impurity in the lanthanum carbonate sample is provided. This X-ray diffraction method preferably uses the Rietveld refinement.

19 Claims, 9 Drawing Sheets

OTHER PUBLICATIONS

Letter (Redacted) from Mylan Inc. to Shire plc et al., "Fosrenol-Lanthanum Carbonate Chewable Tablets (500 mg, 750 mg and 1000 mg), U.S. Patent Nos. 7,465,465; 7,381,428; 5,968,976: Notice of Paragraph IV Certification," Feb. 4, 2009, 48 pages.

Letter (Redacted) from Natco Pharma Limited to Shire Development, Inc. et al., "Lanthanum Carbonate (Equivalent to 500 mg, 750 mg and 1000 mg Lanthanum) Chewable Tablets—Fosrenol®—LVM Reference: 263909," Feb. 13, 2009, 15 pages.

Mineely, Patrick J. et al., "Molten Potassium Pyrosulfate: Reactions of Lanthanum Metal and Six of its Compounds," Aust. J. Chem., 40, 1309-1314, 1987.

Oda, Toshiyuki, "Studies on Crystal Waters of Lanthanum Carbonates," Research Bull. Fac. Edu., Oita University 4(5), (Nat. Sci.), 1975, 5 pages.

"Pharmaceutical Dosage Forms: Tablets," 2nd Ed., vol. 1, Marcel Dekker, Inc., New York, 1989, 53 pages.

Rowe, Raymond C. et al., "Handbook of Pharmaceutical Excipients," 5th Ed., London, Aug. 2005, 8 pages.

*Shire Canada Inc. et al.* v. *Barr Laboratories, Inc.*, "Amended Complaint for Patent Infringement," In the United States District Court for the Southern District of New York, Cause No. 09-Civ-2380 (PGG), Apr. 3, 2009, 15 pages.

*Shire Canada Inc. et al.* v. *Mylan Inc. et al.*, "Complaint for Patent Infringement," In the United States District Court for the Southern District of New York, Cause No. 09 CIV 2555, Mar. 19, 2009, 20 pages.

*Shire Canada Inc. et al.* v. *Natco Pharma Limited*, "Complaint for Patent Infringement," In the United States District Court for the Southern District of New York, Cause No. 09 CIV 3165, Apr. 1, 2009, 13 pages.

Yanagihara, Naohisa et al., "Synthesis of Lanthanide Carbonates," J. of the Less-Common Metals, 167,223-232, 1991, 10 pages.

Mzareulishvili, N. et al., "Study of interaction of lanthanum nitrate with alkali metal ammonium carbonates," Chem. Abstracts, 104(26), No. 236218u, 1986.

Preiss, Josef et al., "Üer die Karbonate der seltenen Erden. I. Bildungsverhältnisse und Hydrolyse der Ceriterdkarbonate," Zeitschrift für Anorganische und Allgemaine Chemie, 131, 275-286, Aug. 22, 1923.

Sklyarenvo et al., "Application of Thernnogravimetry in Analytical Chemistry. Report 3. Thermogravimetry Study of Lanthanum Carbonate," J. Analytical Chemistry - Academy of Science of the USSR, vol. XVI, Issue 4, 1961.

"Long-Term Effect of Lanthanum Carbonate on Bone - Study SPD405-309," Shire Pharmaceutical Development, ClinicalTrials. gov, Aug., 2005, 3 pages http://clinicaltrials.gov/ct2/show/study/NCT00557323?term=spd405-309 (accessed Mar. 17, 2009).

METHOD FOR USE OF LANTHANUM CARBONATE PHARMACEUTICAL COMPOSITIONS

This application claims priority to U.S. patent application Ser. No. 11/418,666, filed May 5, 2006, herein incorporated by reference in its entirety.

1. FIELD OF THE INVENTION

This invention relates to the quantitative analysis of rare earth compounds by X-ray diffraction. More particularly, the assay can be used to determine lanthanum hydroxycarbonate impurities in a lanthanum carbonate composition. The lanthanum hydroxycarbonate may also be made in a purified form for use as a standard.

2. BACKGROUND OF THE INVENTION

Lanthanum carbonate hydrate, which has been used to treat hyperphosphatemia (see, e.g., U.S. Pat. No. 5,968,976) and hyperphosphatemia in patients with renal failure (see, e.g., JP 1876384), is a molecule which is prone to decarboxylation under certain stressful conditions such as high heat and elevated humidity. These conditions may be present during the manufacture of lanthanum carbonate hydrate or during the storage of the unformulated or formulated material. The decarboxylation product is lanthanum hydroxycarbonate.

Hyperphosphatemia is a particular problem of patients with renal failure, using dialysis equipment. Conventional dialysis fails to reduce levels of phosphate in the blood, so that the levels rise in time. It is known to control phosphate levels by the oral administration of aluminium salts, or calcium salts. With the known toxic effects of aluminium, aluminium-based therapy tends to be avoided. In the case of calcium salts, calcium is absorbed rather readily from the gut, and in turn causes hypercalcaemia.

Certain forms of lanthanum carbonate have been used to treat hyperphosphatemia in patients with renal failure (see, e.g., JP 1876384). U.S. Pat. No. 5,968,976, owned by the assignee of the present invention, describes the preparation and use in a pharmaceutical composition of certain hydrates of lanthanum carbonate for the treatment of hyperphosphatemia.

U.S. Pat. No. 5,968,976 teaches that certain forms of lanthanum carbonate exhibit improved performance in a variety of tests, over standard commercial lanthanum carbonate, which is believed to be the octahydrate form, and over $La_2(CO_3)_3 \cdot xH_2O$ or similar compounds. U.S. Pat. No. 5,968,976 teaches the use of lanthanum carbonate of formula $La_2(CO_3)_3 \cdot xH_2O$ where x has a value from 3 to 6, preferably from 3.5 to 5, more especially from 3.8 to 4.5, for the preparation of a medicament for the treatment of hyperphosphatemia by administration into the gastrointestinal tract. Also provided is a pharmaceutical composition comprising said lanthanum carbonate, in admixture or association with a pharmaceutically acceptable diluent or carrier, in a form for administration into the gastrointestinal tract for the treatment of hyperphosphatemia. Also provided is a method of treatment of hyperphosphatemia in a patient with renal failure, comprising the administration of an effective dose of said lanthanum carbonate into the gastrointestinal tract. Also provided is administration by an oral route.

It is a regulatory requirement that analytical methods be developed to quantify the amount of degradation products which may be present in a pharmaceutical agent and a pharmaceutical product. Typically, this is done using a chromatographic technique such as high performance liquid chromatography (HPLC), which requires dissolution of test samples in the appropriate solvent.

Both $La_2(CO_3)_3$ and $LaCO_3OH$ are insoluble in water and standard organic solvents. Either may be dissolved in acidic solution, but in doing so, reactions occur which form impurities in the sample. For example, dissolution of either $La_2(CO_3)_3$ or $LaCO_3OH$ in aqueous hydrochloric acid results in a solution of lanthanum chloride, ($LaCl_3$). Since both materials give the same product after dissolution of a sample in acid, there is no way to distinguish $La_2(CO_3)_3$ from $LaCO_3OH$. Similarly, the same salt is formed when either material is dissolved in other aqueous acids. Because of the insolubility of $La_2(CO_3)_3$ and $LaCO_3OH$ in standard solvents, and the fact that each substance reacts to form the same material in acidic solvents, chromatographic techniques such as HPLC cannot be used to develop quantitative methods to monitor the presence of degradants.

It is conceivable that dissolution in aqueous acid and titration of the resulting solution for lanthanum content could be a technique used to quantify the amount of $LaCO_3OH$ in $La_2(CO_3)_3$ hydrate. However, this is impractical because the lanthanum content of both species is very similar. For example, $LaCO_3OH$ contains 64.3% La, $La_2(CO_3)_3$ tetrahydrate contains 52.4% La, and a mixture of 1% $LaCO_3OH$ in $La_2(CO_3)_3$ tetrahydrate would contain 52.5% La. Thus, one would be unable to distinguish pure pharmaceutical agent from pharmaceutical agents containing, for example, 1% degradant, which is an amount of degradant in excess of amounts typically allowed by regulations.

Various techniques might be used to develop quantitative analytical methods for analysis of solid mixtures. Examples of these techniques include differential scanning calorimetry, infrared spectroscopy, Raman spectroscopy, XRPD, solid-state nuclear magnetic resonance spectroscopy, and dynamic vapor sorption. The first criterion that must be met by an analytical technique to render it usable for method development is specificity. That is, the technique must be able to differentiate the analyte from the matrix (i.e. $LaCO_3OH$ from the pharmaceutical agent $La_2(CO_3)_3$ hydrates and $LaCO_3OH$ from $La_2(CO_3)_3$ hydrates when the sample additionally contains other excipients and/or carriers). However, most of these techniques are not capable of differentiating $LaCO_3OH$ from $La_2(CO_3)_3$ hydrates.

A technique capable of differentiating $LaCO_3OH$ from $La_2(CO_3)_3$ hydrates is x-ray powder diffraction (XRPD). Normally XRPD is a technique which is used to characterize materials and detect differences in crystal structure (such as polymorphs). It is therefore usually used in the identification of structures and is not normally used to quantify materials in the sense of an impurity or degradant assay.

Therefore, there is a need in the art to quantitatively determine the scope of material degradation and to quantifiably determine the level of purity of the degradation products of a rare earth compounds such as $CaOHCO_3$ compared to the rare earth compound itself (i.e., $La_2(CO_3)_3$).

3. SUMMARY OF THE INVENTION

In accordance with the present invention, provided herein is a method of treating hyperphosphatemia in a subject comprising:

(i) obtaining a crude lanthanum carbonate composition comprising lanthanum carbonate having the formula $La_2(CO_3)_3 \cdot xH_2O$ wherein x has a value from 3 to 6 and at least one impurity (e.g., a lanthanum hydroxy carbonate impurity);

(ii) subjecting the crude lanthanum carbonate to a purity assay comprising the steps:
   (a) obtaining an X-ray diffraction pattern of the crude lanthanum carbonate composition;
   (b) obtaining a plurality of reference samples containing the impurity or impurities;
   (c) obtaining a plurality of X-ray diffraction patterns of the reference samples; and
   (d) performing Rietveld analysis on the X-ray diffraction patterns to obtain:
      the detection limit, minimum quantitation limit (MQL), and/or upper analytical limit from the reference samples and
      the predicted impurity concentration value from the crude lanthanum carbonate composition pattern, (iii) when the lanthanum carbonate composition contains at least one impurity above the limit of detection according to the assay of (ii), purifying the lanthanum carbonate composition and repeating step (ii); and (iv) administering to said subject an amount of the lanthanum carbonate composition effective to treat said hyperphosphatemia.

In one embodiment, x in the formula $La_2(CO_3)_3 \cdot xH_2O$ has a value from 3.5 to 5. In another embodiment, x has a value from 3.8 to 4.5. The administration may be by an oral route.

In another embodiment, the impurity comprises lanthanum hydroxycarbonate ($La(CO_3)OH$), which may comprise a combination of $La(CO_3)OH$ form (I) and form (II). In yet another embodiment, the lanthanum carbonate composition administered in step (iv) comprising 0.55% or less lanthanum hydroxycarbonate (I). The lanthanum hydroxycarbonate (I) is preferably characterized by an X-ray powder diffraction pattern having peaks at approximately 17.7°, 24.4°, and 30.3° two theta.

In another embodiment, the amount of lanthanum hydroxycarbonate administered in step (iv) is up to 0.55% lanthanum hydroxycarbonate form (I) and up to 0.29% lanthanum hydroxycarbonate form (II). The lanthanum carbonate composition administered in step (iv) may comprise at least 68% $La_2(CO_3)_3 \cdot 4H_2O$, or it may comprise at least 95% pure lanthanum carbonate, or it may comprise at least 99% pure lanthanum carbonate.

In another embodiment, the present invention provides a method of treating hyperphosphatemia in a subject comprising:

(i) obtaining a crude lanthanum carbonate composition;

(ii) measuring the purity of the lanthanum carbonate composition, wherein the measuring comprises:
   (a) obtaining an X-ray diffraction pattern of the crude lanthanum carbonate composition;
   (b) obtaining a plurality of reference samples containing lanthanum hydroxy carbonate;
   (c) obtaining a plurality of X-ray diffraction patterns of the reference samples; and
   (d) performing Rietveld analysis on the X-ray diffraction patterns to obtain the predicted lanthanum hydroxy carbonate concentration value from the crude lanthanum carbonate composition pattern, (iii) administering to said subject an amount of the lanthanum carbonate composition containing 0.55% or less lanthanum hydroxycarbonate (I) as predicted by step (ii) wherein said lanthanum carbonate composition is effective to treat said hyperphosphatemia.

Another embodiment comprises a method of assaying the purity of a rare earth compound having at least one known impurity, wherein at least one of the salt or impurity is a compound that disassociates in aqueous media, comprising:

(i) obtaining an X-ray diffraction pattern of the salt;

(ii) obtaining a plurality of reference samples containing the impurity or impurities;

(iii) obtaining a plurality of X-ray diffraction patterns of the reference samples; and (iv) performing Rietveld analysis on the X-ray diffraction patterns to obtain:
   the detection limit, minimum quantitation limit (MQL), and/or upper analytical limit from the reference samples and
   the predicted impurity concentration value from the rare earth compound pattern.

In one embodiment, the rare earth compound is a lanthanum carbonate composition and the known impurity is one or more polymorph of lanthanum hydroxycarbonate.

In another embodiment, the method further comprises (v) classifying the predicted concentrations as:
   below the detection limit,
   between the detection limit and the MQL,
   between the MQL and upper analytical limit, and
   greater than the upper analytical limit;

(vi) for samples having a predicted concentration between the detection limit and the MQL, performing a visual analysis of the XRPD patterns; and (ix) optionally reporting purity or impurity level.

The present invention also provides a method of preparing a lanthanum carbonate comprising:

(i) preparing a crude lanthanum carbonate;

(ii) subjecting the crude lanthanum carbonate to a purity assay comprising the steps:
   (a) obtaining an X-ray diffraction pattern of the salt;
   (b) obtaining a plurality of reference samples containing the impurity or impurities;
   (c) obtaining a plurality of X-ray diffraction patterns of the reference samples; and
   (d) performing Rietveld analysis on the X-ray diffraction patterns to obtain:
      the detection limit, minimum quantitation limit (MQL), and/or upper analytical limit from the reference samples and
      the predicted impurity concentration value from the rare earth compound pattern, (iii) when the lanthanum carbonate contains lanthanum hydroxycarbonate above the limit of detection according to the assay of (ii), purifying the lanthanum carbonate and repeating step (ii).

The present invention also provides a pharmaceutical composition comprising lanthanum hydroxycarbonate form (I) characterized by an X-ray powder diffraction pattern having reflections at approximately 17.7, 24.4, and 30.3° two theta, wherein the lanthanum hydroxycarbonate content of the composition comprises at least 96% lanthanum hydroxycarbonate form (I). Preferably, the two theta values will be within ±0.2° of the listed values, and more preferably, the two theta values will be within ±0.1° of the listed values. More preferably, the composition comprises at least 98% lanthanum hydroxycarbonate form (I), and even more preferably, the composition comprise at least 99% lanthanum hydroxycarbonate form (I).

4. BRIEF DESCRIPTION OF THE DRAWINGS

5. DETAILED DESCRIPTION OF THE INVENTION

5.1. General Definitions

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Examples of such limitations include preparing the sample in a wet versus a dry environment, different instruments, variations in sample height, and differing requirements in signal-to-noise ratios. For example, "about" can mean a range of up to 20% of a given value, and more preferably means a range of up to 10%. Alternatively, particularly with respect to biological systems or processes, the term can mean within an order of magnitude, preferably within 5-fold, and more preferably within 2-fold, of a value.

"Lanthanum carbonate" as used herein encompasses all polymorphs of hydrated forms of lanthanum carbonate and of anhydrous lanthanum carbonate.

The term "hydrated lanthanum carbonate" refers to lanthanum carbonate having water content approximately equivalent to 4-5 moles of water.

Figure 1:
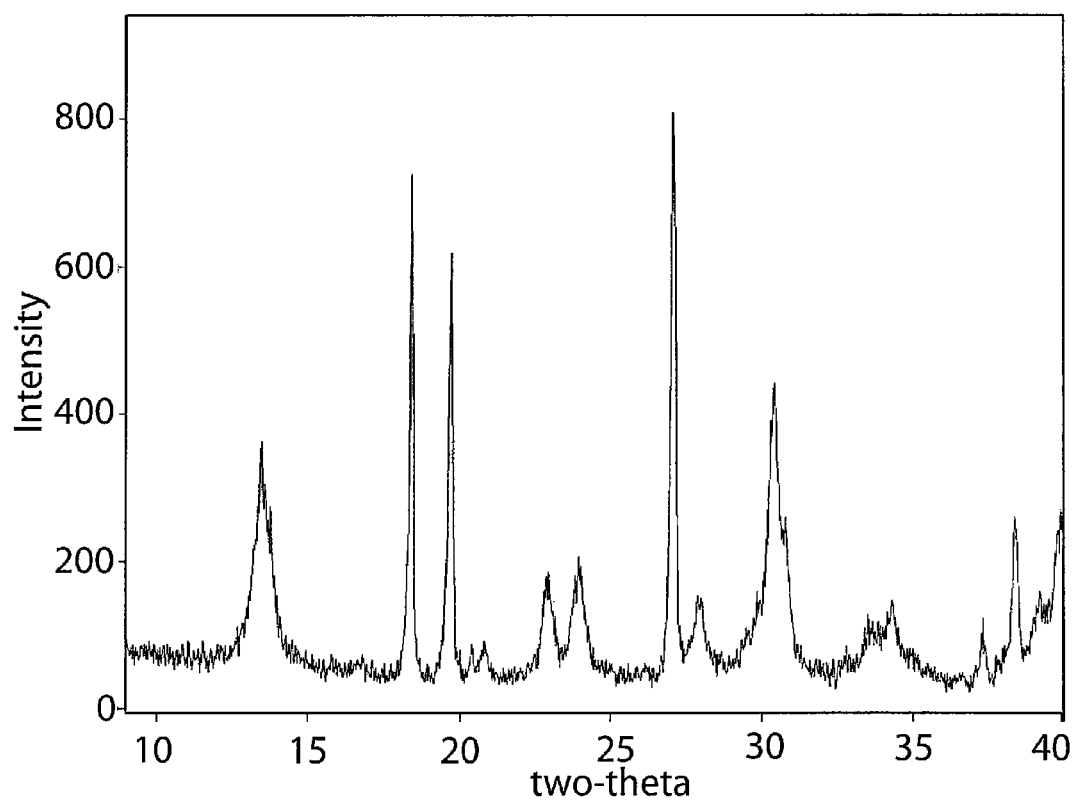
FIG. 1 is an XRPD (x-ray powder diffraction) pattern of $La_2(CO_3)_3 \cdot 4H_2O$.
Figure 2:
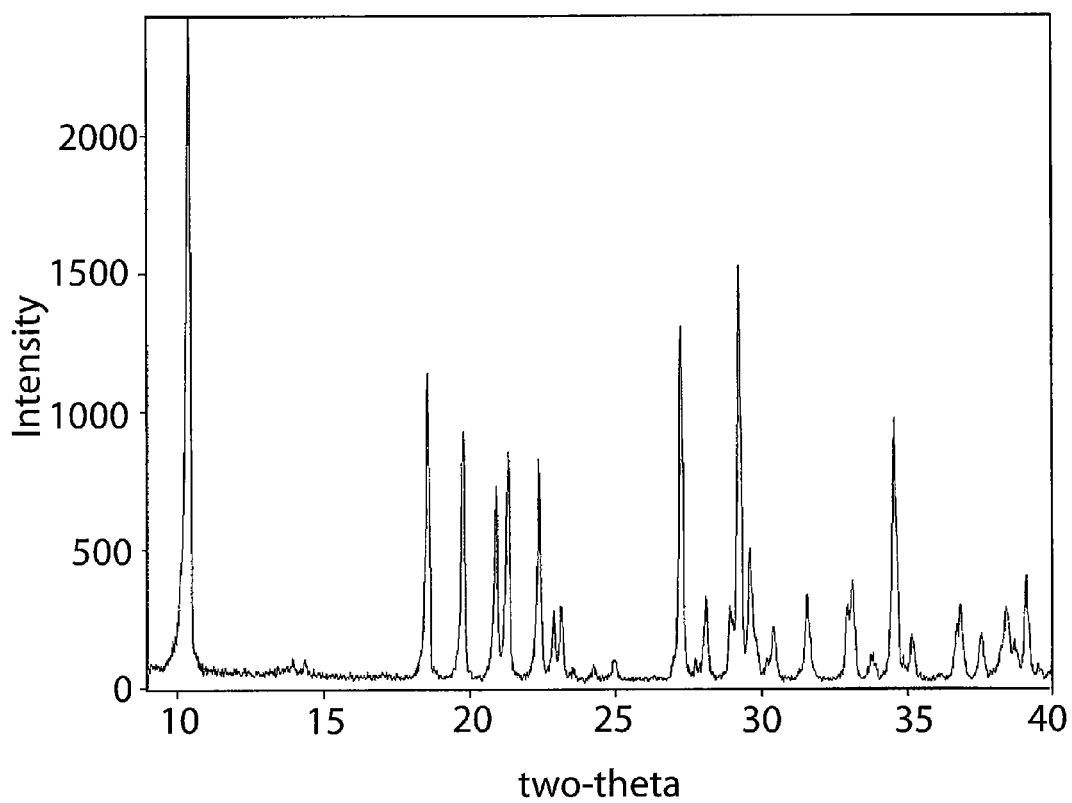
FIG. 2 is an XRPD pattern of $La_2(CO_3)_3 \cdot 8H_2O$.
Figure 3:
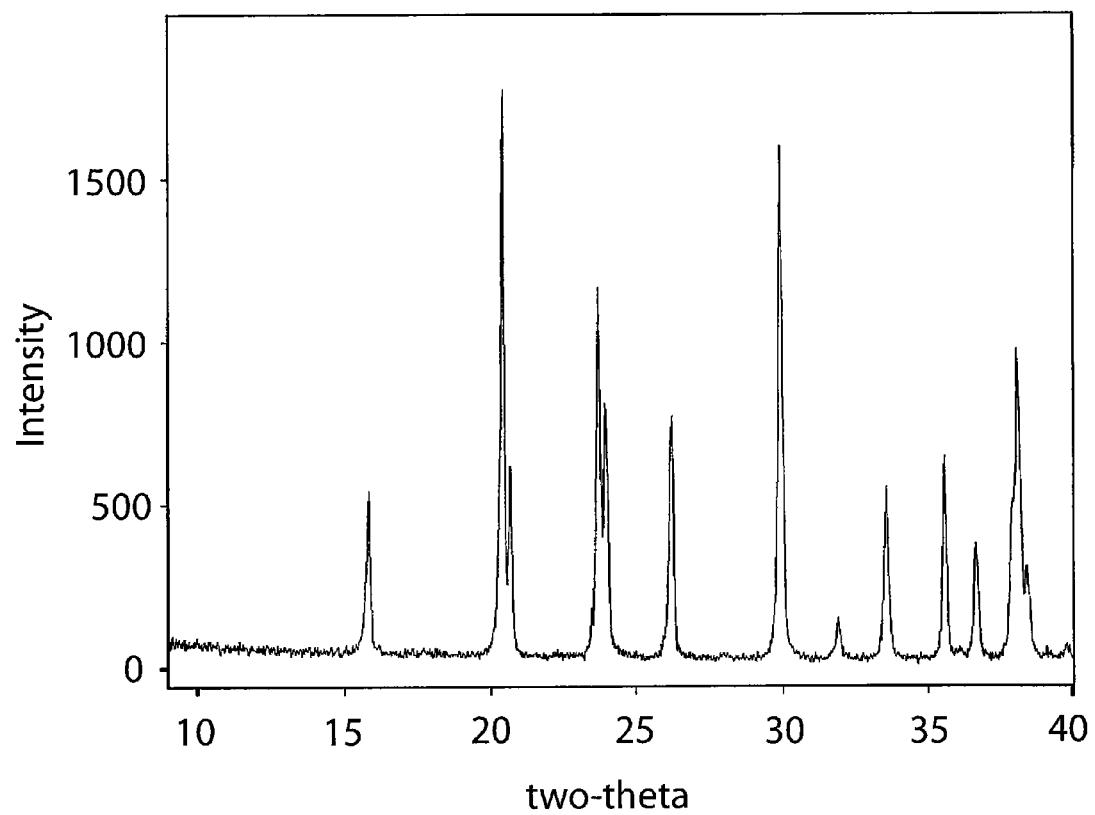
FIG. 3 is an XRPD pattern of $La(CO_3)OH$ form (II).
Figure 4:
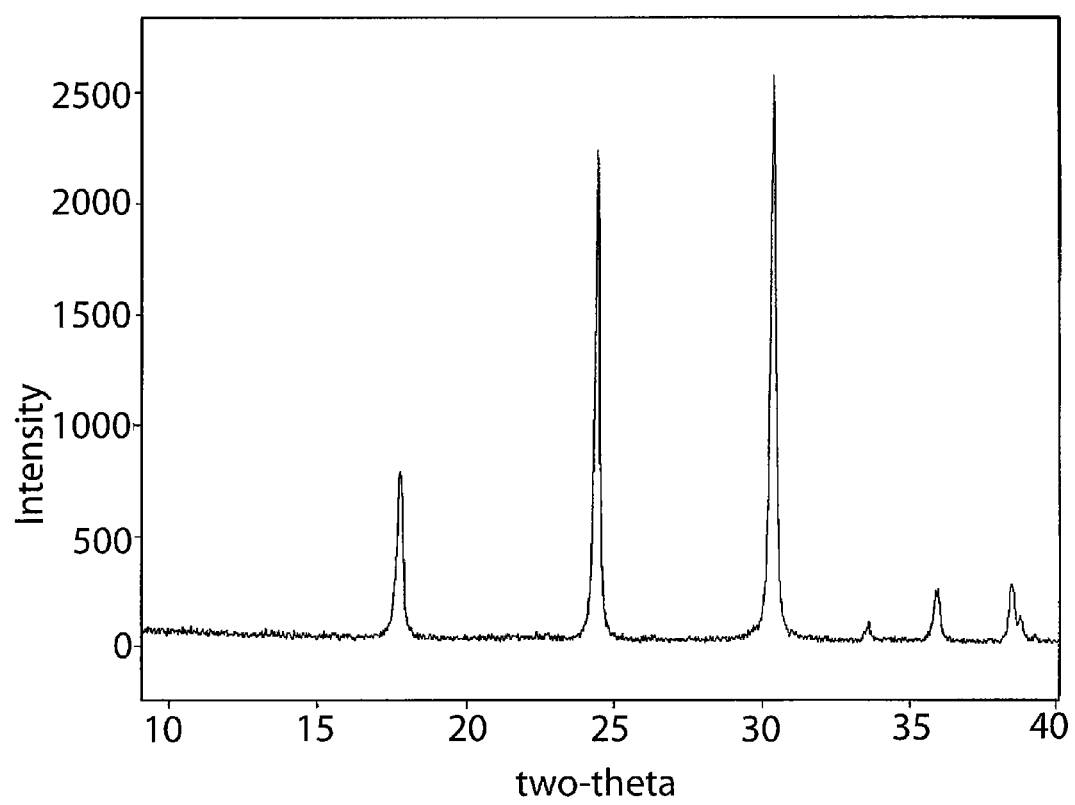
FIG. 4 is an XRPD pattern of $La(CO_3)OH$ form (I).

"Lanthanum hydroxycarbonate" as used herein encompasses all polymorphs of lanthanum hydroxycarbonate, including form (I) and form (II). The term HC(I) refers to lanthanum hydroxycarbonate polymorphic form (I) as described by the XRD pattern in FIG. 4. The term HC(II) refers to lanthanum hydroxycarbonate polymorphic form (II) as described by the XRD pattern in FIG. 3.

The phrase "rare earth compound" as used herein refers to a compound containing at least one rare earth element of the lanthanide series, yttrium, scandium, and thorium. The lanthanide series comprises cerium, praseodymium, neodymium, samarium, europium, gadolinium, terbium, dysprosium, holmium, erbium, thulium, ytterbium, and lutetium. Each of these elements closely resemble lanthanum in their chemical and physical properties, each having similar so that any given compound of the rare earths is likely to crystallize with the same structure as any other rare earth. Similar salts of these metals will have common properties including reacting with water to liberate hydrogen, binding to water, and acting as strong reducing agents.

"Percent" or "%" as used herein refers to the percentage by weight of the total composition unless otherwise noted.

The term "substantially pure," when referring to either lanthanum carbonate or lanthanum hydroxycarbonate, refers to the lanthanum compound having about 90% purity or greater, on an anhydrous basis. Preferably, the purity is about 95% or greater; more preferably, the purity is 98% or greater; even more preferably, the purity is 99% or greater. It is preferred that the purity is 99.2% or greater; more preferably, the purity is 99.4% or greater; even more preferably, the purity is 99.6%; even more preferably, the purity is 99.8% or greater; and even more preferably, the purity is 99.9% or greater.

The term "salt" is used herein refers to the ionic product of a reaction between a metallic oxide and an acid. The salts useful in the present invention are salts of rare earth elements such as lanthanum.

The term "lanthanum salt" as used herein refers to lanthanum bound to a negatively charged anion to create a neutral species. Examples of hydrolysable lanthanum salts include, but are not limited to lanthanum methoxyethoxide, lanthanum acetate, lanthanum acetylacetonate, lanthanum oxalate, and hydrates thereof . . . . Preferably, the hydrolyzable lanthanum salt is a lanthanum (III) salt.

The phrase "a compound that disassociates in aqueous media" as used herein means that at least some of the compound separates into two or more components such as $La_2(CO_3)_3$ separating into $La^{3+}$ and $CO_3^{2-}$ This disassociation may be induced by an acidic environment (e.g., aqueous HCl) and may be followed by the formation of salts such as $LaCl_3$.

The phrases "Rietveld analysis" and "Rietveld method" as used herein mean the data is analyzed using the constrained, full pattern analytical model first developed by Rietveld (*Acta. Crystallogr.*, 22, 151-2, 1967, and *J. Appl. Crystallogr.*, 2, 65-71, 1969). Constrained analysis means that the analytical model is limited, or constrained, using one or more parameters obtained from chemical or other information about the sample. In particular, the assay for the impurity lanthanum hydroxycarbonate in a lanthanum carbonate sample may be constrained using the knowledge of the crystal structure of the components in the sample: lanthanum carbonate tetrahydrate, other lanthanum carbonate hydrates, lanthanum hydroxycarbonate form (I) and lanthanum hydroxycarbonate form (II). A full-pattern analysis is one in which the full XRD pattern in analyzed instead of only the more intense peaks. The full pattern encompasses a range of two-theta values, and may include, for example, the range from 9 to 40° 2θ, or from 10 to 35° 2θ. Full-pattern analysis can be used to provide greater accuracy and precision to the quantitative analysis than a peak-intensity based method. The phrases "Rietveld analysis" and "Rietveld method" also include analyses using a modification of the Rietveld method, such as those described by Bish, D. L. and Howard, S. A. 1988 (*J. Appl. Crystallog-* raphy, 21, 86-91). Other modifications of the Rietveld method are also contemplated as within the scope of the Rietveld analysis.

5.2. Lanthanum Carbonate and Lanthanum Hydroxycarbonate

Lanthanum carbonate has the general formula $La_2(CO_3)_3 \cdot xH_2O$, wherein x has a value from 0 to 10. A common form of the hydrate has an average x value of about between 3 and 5. The hydration level of the lanthanum compound can be measured by methods well known in the art, such as thermo gravimetric analysis (TGA) or x-ray powder diffraction (XRPD).

Lanthanum carbonate has a tendency to degrade via decarboxylation to lanthanum hydroxycarbonate as shown:

$$La_2(CO_3)_3 + nH_2 \rightarrow 2LaOHCO_3 + CO_2 + (n-1)H_2O$$

Subjecting $La_2(CO_3)_3$ hydrate to hydrothermal conditions (water at high temperature and pressure) affords lanthanum hydroxycarbonate ($LaCO_3OH$). (Aumont, R.; Genet, F.; Passaret, M.; Toudic, Y. *C.R. Acad. Sci. Paris Ser. C* 1971, 272, 314; Christensen, A. N. *Acta Chem. Scand.* 1973, 27, 2973; Haschke, J. M. *J. Solid State Chem.* 1975, 12, 115). The same reaction occurs under relatively mild conditions such as heating a water slurry of $La_2(CO_3)_3$ hydrate under ambient pressure at 77° C. for 20 hours followed by 97° C. for 1.5 hours (Sun, J.; Kyotani, T.; Tomita, A. *J. Solid State Chem.* 1986, 65, 94). It is known that $LaCO_3OH$ exists in two polymorphic forms (I) and (II) (id.)

This process is accelerated in the presence of moisture or heat and appears to be self-catalyzing. Hence, even a very small amount of lanthanum hydroxycarbonate in lanthanum carbonate formulations causes rapid and excessive degradation.

Further, conditions sufficient to bring about decarboxylation of these materials may be present during their manufacture as well as during storage in a formulated or unformulated state. Thus, there is a possibility that $La_2(CO_3)_3$ hydrate used as an active pharmaceutical ingredient would contain the degradation product $LaCO_3OH$, either as polymorph (I) or polymorph (II).

Lanthanum carbonate tetrahydrate and octahydrate can be made by methods known in the art including the method described in U.S. Pat. No. 5,968,976.

The degradation of lanthanum carbonate into lanthanum hydroxycarbonate can be observed by examining an XRPD pattern of a potentially degraded lanthanum carbonate sample. The presence of observable peaks corresponding to lanthanum hydroxycarbonate in the sample pattern indicates degradation whereas the absence of observable peaks indicates no detectable degradation.

Generally, lanthanum hydroxycarbonate may be synthesized by methods known in to those skilled in the art including, (1) from hydrated lanthanum(III) carbonate under hydrothermal conditions as disclosed in Haschke, J., *J. Solid State Chemistry*, 12 (1975) 115-121; (2) from $LaBr(OH)_2$ treated with carbon dioxide or from hydrolysis of lanthanum carbonate as disclosed in Sun, J.; Kyotani, T.; Tomita, A. *J. Solid State Chem.*, 65 (1986) 94; (3) the treatment of lanthanum (III) nitrate with urea or thiourea as disclosed in Han et al. *Inorganic Chemistry Communications*, 6 (2003) 117-1121; (4) the treatment of lanthanum(III) chloride with urea or thiourea as disclosed in Han et al. *Journal of Solid State Chemistry*, 177 (2004) 3709-3714; (5) the treatment of lanthanum(III) chloride with trifluoroacetic acid as disclosed in Wakita, H et al., *Bulletin of the Chemical Society of Japan*, 52 (1979) 428-432; or (6) the treatment of lanthanum(III) chloride with sodium carbonate as disclosed in Nagashima, K et al. *Bulletin of the Chemical Society of Japan*, 46 (1973) 152-156.

5.3. Rare Earth Compounds

Other rare earth compounds will degrade or react to form impurities in the product sample. For example, compounds such as lanthanum citrate, acetate, lactate methoxyethoxide, acetylacetonate, oxalate, and hydrates thereof may be analyzed in the same manner as disclosed herein for the lanthanum carbonate.

For example, lanthanum acetate will degrade to form a hydroxy derivative (i.e., $La(OAc)_{3-x}$ $(AcAc)_x$, will hydrolyzed into $La(AcAc)_{3-x}(OH)_x$ (Yin, M Z et al., *J Zhejiang Univ Sci.* 2004 5(6), 696-8)). It is contemplated that concentrations of lanthanum hydroxyacetate impurities can be determined in the same or similar manner as described herein for lanthanum hydroxycarbonate by replacing the hydroxycarbonate standards with hydroxyacetate standards and modifying the parameters used in the Rietveld analysis for the crystal of the hydroxyacetate isoform(s).

Similarly, lanthanum citrate (i.e., $La(Hcit)(H_2O)]_n$ where $(Hcit^{3-})$ is $C(OH)(COO^-)(CH_2COO^-)_2)$ can hydrolyze to form a hydroxy derivative. Lanthanide citrate has a structure comprising chains of La(III) cations bridged by O—C—O groups with pendant Hcit anions; the Hcit ligand is involved in six La—O bonds to five different La centers. (Baggio R, Perec M. *Inorg Chem.* 2004; 43(22), 6965-8). It is contemplated that concentrations of lanthanum hydroxycitrate impurities can be determined in the same or similar manner as described herein for lanthanum hydroxycarbonate by replacing the hydroxycarbonate standards with hydroxycitrate standards and modifying the parameters used in the Rietveld analysis for the crystal of the hydroxycitrate isoform(s).

Other rare earth salts will degrade similarly to lanthanum salts since these elements closely resemble lanthanum in their chemical and physical properties. Therefore, some degradation impurities of other rare earth salts may also be analyzed using the XRD analysis method of the present invention for other rare earth metal salts. To determine whether the degradation product and the compound such as those discussed above can be analyzed by the method of the present invention, an XRD of both the compound and the degradation product must be obtained and the parameters used in the Rietveld analysis for the crystal structures must be obtained as appropriate for the compounds used, as described herein for the parameters used for analysis of lanthanum hydroxycarbonate. The two spectra must differ in at least one structural feature. Preferably, this feature will comprise a number of unique positions (2 theta) and intensities.

5.4. Preparation of Substantially Pure Compounds

To prepare standards for the assay of the present invention, substantially pure forms of each of the compounds and polymorphs must be made. These samples are then used to prepare reference samples containing a varying amount of each of the different components of the sample. In one embodiment, the reference samples will span a range from 0-50% of the impurity (each polymorph if more than one polymorph is in the sample), or more preferably 0-30%. In another embodiment, the reference samples span only a narrow range of, for example, 0-10% of the impurity. The standards are used to calibrate the scale factors in the analytical model described herein.

For the more stable of the two lanthanum hydroxycarbonate polymorphs, form (II), the production of a substantially pure sample is accomplished by the methods known in the art. However, the production of polymorph (I) is not as simple since this compound is not soluble in many of the organic solutions commonly used for recrystallizing and forming different polymorphs.

Factors important to the synthesis of hydroxycarbonate polymorph (I) include temperature, humidity, the presence of unreacted $La(OH)_3$, reaction scale, and the particle size of the starting material.

An attempt was made to convert polymorph (II) to polymorph (I) by heating in water for an extended period of time. No evidence of conversion was seen after 18 days at 90-100° C. Experiments in which $La_2(CO_3)_3 \cdot 8H_2O$ was treated with $La(OH)_3$ in water afforded either a mixture of $LaCO_3OH$ polymorphs (I) and (II) or $LaCO_3OH$ polymorph (II) and unreacted $La_2(CO_3)_3 \cdot 8H_2O$.

Decarboxylation of either $La_2(CO_3)_3 \cdot 4H_2O$ or $La_2(CO_3)_3 \cdot 8H_2O$ in the presence of water alone afforded either wholly or predominantly polymorph form (II). The presence of hydroxide ion during decarboxylation of $La_2(CO_3)_3 \cdot 8H_2O$ can favor production of $LaCO_3OH$ polymorph (I). However, production of form (I) with additional $OH^-$ is inconsistent.

It was also noted that decarboxylation of $La_2(CO_3)_3 \cdot 8H_2O$ under a carbon dioxide atmosphere gave some polymorph (I). This would be expected if the carbon dioxide inhibited the reaction giving polymorph (II) and allowed the reaction giving polymorph (I) to occur at reflux.

Ammonium carbonate was therefore used as an additive to liberate carbon dioxide as it was heated, providing a constant source of the inhibitor of the reaction leading to polymorph (II). Indeed, the major product in most of these reactions was polymorph (I). By using an amount of ammonium carbonate which was approximately 25% of the weight of $La_2(CO_3)_3 \cdot 8H_2O$, the formation of polymorph (II) was completely suppressed and the product was pure polymorph (I).

This substantially pure form (I) can then be used to create a standard used in the Rietveld analysis of the content of $LaCO_3OH$ form (I) in a sample. Additionally, this polymorph is useful as a pharmaceutical agent. Similar to the carboxylated salt, $LaCO_3OH$ form (I) can be used to treat hyperphosphatemia. The substantially pure compound can optionally be mixed with one or more pharmaceutically acceptable carrier or excipient and used in the manner described for $La_2(CO_3)_3$ hydrate.

Similarly, substantially pure form (II) can be used as both a standard used for the Rietveld analysis to determine the content of $LaCO_3OH$ form (II) in a sample and as a pharmaceutical agent, such as an agent for the treatment of hyperphosphatemia. This isoform can be administered to a patient as an active agent or in a pharmaceutical composition without also administering form (I) or other impurities to the patient as well. In addition, a pharmaceutical agent containing a known mixture of form (I) and form (II) $LaCO_3OH$ can be formed and used for treating hyperphosphatemia.

5.5. Analysis Model

Quantitative analytical methods were developed for pharmaceutical agents and drug products based on XRPD measurements. The method of data modeling initially selected was a chemometric one called partial least squares (PLS) analysis. PLS is a statistical approach that results in an equation (model) that describes the correlation between composition and multiple measured variables. The PLS algorithm examines user-specified regions of the calibration data to determine which areas are varying statistically as a function of component concentration. The number of variables can be large, so whole-pattern models can be generated that utilize all measured data. For results from a model of this type to be accurate, the data obtained from a test sample need to 'fit' the model. Any data obtained that are outside of the range allowed for those data by the model may cause inaccuracy. Goodness-of-fit metrics like the spectral F ratio provide a measure of how well measured data fit the model. PLS is a useful approach when the components to be monitored experience severe overlap with other components in the mixture, when the correlation between concentration and absorbance is very complex, or when additional components whose concentrations are unknown may be present in the sample mixture. Since PLS is a statistical analysis technique, a large number of standards are needed in order to correlate the analytical data with concentration.

As samples were being analyzed using XRPD data with a PLS model, the goodness-of-fit metric was found to be outside the established threshold in some cases. Investigation revealed that the XRPD patterns were somewhat different in the problem samples compared to the patterns of the materials used to generate the PLS model. An investigation of the pattern differences was undertaken, necessitating an understanding of the crystal structures of the component substances of the mixtures.

The structures of $La_2(CO_3)_3$ tetrahydrate, $LaCO_3OH$ polymorph (I), and $LaCO_3OH$ polymorph (II) were not available in the literature. The present invention provides structural models of the latter three materials based on XRPD data and the structures of similar materials in the literature. It was found that $La_2(CO_3)_3$ tetrahydrate is a layered structure in which the layers consist of $La_2(CO_3)_3$ species with water bound between the layers. On the other hand, both polymorphs of $LaCO_3OH$ are strongly bonded in all three dimensions. The result is that $La_2(CO_3)_3$ tetrahydrate breathes with increasing or decreasing amounts of water; the layers are further apart with increasing amounts of water. This breathing affects both the shape and intensity of the main reflection specific for tetrahydrate in the XRPD pattern. Because PLS methods are extremely sensitive to these sorts of changes, the initial PLS models created using one type of tetrahydrate material could not be used to predict mixture concentrations that contained a different tetrahydrate material. These differences in the tetrahydrate materials became apparent when samples were submitted for analysis via the PLS methods and the unexpected results were obtained. The differences observed in the XRPD patterns of samples being analyzed were consistent with small changes in layer separation expected with changes in the amount of contained water. Note that the changes in the amount of water were not sufficient to render the $La_2(CO_3)_3$ tetrahydrate samples out of specification as far as water content. The crystal structure of $La_2(CO_3)_3$ octahydrate is known, (Shinn, D. B.; Eick, H. A. *Inorg. Chem.* 1968, 7, 1340), and data from this structure can be used in the Rietveld analysis.

It was found that the problem exhibited by PLS data modeling could be overcome using another full-spectrum model, Rietveld analysis. This methodology was originally proposed by H. M. Rietveld for determining structural parameters from XRPD data. (Rietveld, H. M. J. *Appl. Crystallogr.* 1969, 2, 65). Three dimensional structures of crystalline materials are typically deduced from x-ray studies of single crystals, but when single crystals are not available, the Rietveld method can be used to deduce the structures from XRPD data and thereby used to constrain the data. By substituting Rietveld analysis for PLS analysis, the method was made robust relative to the differences observed in XRPD data sample-to-sample. The Rietveld method varies structural factors derived from the crystal structures in order to generate the best fit of measured and calculated XRPD patterns. Since the structure of $La_2(CO_3)_3$ tetrahydrate does not change sample-to-sample, but only expands or contracts based on water content, Rietveld treatment can model the layer separation differences based on the underlying structure.

The Rietveld method then minimizes the least square residual:

$$R = \sum_j w_j |I_{j(o)} - I_{j(c)}|^2$$

where $I_{j(o)}$ and $I_{j(c)}$ are the intensity observed and intensity calculated by the Rietveld refinement, respectively, at the jth step in the data, and wj is the weight.

The refinement iteratively fits to the data by modifying the structure and instrument parameters.

This method is also advantageous because it uses the whole XRD pattern instead of a number of selected peaks. This, although increasing the calculation time, provides for much greater accuracy and precision of the fit.

Further information on this method can be found in Rietveld, H. M. "Line Profiles of Neutron Powder-diffraction Peaks for Structure Refinement." *Acta. Crystallogr.*, 22,151-2, 1967, and Rietveld, H. M., "A Profile Refinement Method for Nuclear and Magnetic Structures." *J. Appl. Crystallogr.*, 2, 65-71, 1969, each of which are herein incorporated by reference.

In a preferred embodiment, the results returned from the Rietveld analysis are based on the following criteria:

| Predicted Concentration | Reported Value |
| --- | --- |
| <LOD | "non-detectable, complies" |
| LOD – MQL | user input needed |
| MQL-upper analytical limit | report concentration, "does not comply" |
| >upper analytical limit | >upper analytical limit, "does not comply" | where LOD is the limit of detection, or detection limit, given at a 99% confidence limit. MQL is the minimum quantitation limit, which may also be defined as the limit of quantitation (LOQ) is the limit at which accurate quantitation is possible. MQL may be expressed as $10(\sigma/S)$, where car is the standard deviation of the observed response of samples free of analyte and S is the slope of the response curve.

If the predicted concentration is between the LOD and the MQL, then the individual XRDP patterns should be co-added (when more than one XRDP was obtained) and visually examine for the presence of hydroxycarbonate versus the hydroxycarbonate reference patterns. Report either "Detected Rietveld, none detected visual-complies" or "Detected Rietveld and visual—does not comply".

The assay of the present invention preferably follows the analytical guidelines provided by the International Committee on Harmonization (1CH) document (November 1996) "Guidance for Industry, Q2B Validation of Analytical Procedures: Methodology." These guidelines include limitations on specificity, linearity and range, precision, detection limits, minimum quantitation limits, accuracy of the validation standards, system suitability, and ruggedness.

5.6 Pharmaceutical Compositions

The assay of the present invention is particularly useful since it is able to analyze impurity content of an active agent in the presence of excipients. As discussed below, a tablet form of lanthanum carbonate can be tested for the relative weight percent of the hydroxycarbonate polymorphs. These excipients do not significantly interfere with the analytical measurements.

Pharmaceutical compositions for oral administration according to the invention may be formulated and manufactured using methods well known in the art. Suitable diluents or carriers are also well known. The compositions may desirably be in a dosage form, to provide a single daily dose, or a number of sub-daily dosages. Conventional pharmacological methods may be used to ascertain suitable dose levels. The level of phosphate in the food that an individual ingests is important. Daily dosages are indicated to be in the range 0.1 to 50 g, preferably about 0.5 to 15 g. Suitable forms for oral administration include solid forms such as tablets, capsules and dragees and liquid forms such as suspensions or syrups. In addition to diluents and carriers, it is conventional in the formulation of oral preparations to include non-active ingredients such as thickeners, taste-improving components and colouring agents. The said carbonate may also be coated or treated to provide delayed-release forms. Preferably, the required daily dosage is given in tablet form, eg chewable tablet form, to be taken with meals. A suitable daily dosage of about 2 g for 70 kg man, should be compared with a daily dosage of 20 g for a commercial calcium-based phosphate binding composition.

6. EXAMPLES

Example 6.1

Preparation of Pure Hydroxycarbonate Polymorph (II)

The starting material, $La_2(CO_3)_3 \cdot 4H_2O$, was provided by Shire Pharmaceutical and was analyzed by XRPD to confirm its identity. A mixture of about 1500 g (2.8 mol) of $La_2(CO_3)_3 \cdot 4H_2O$ and 10 liters of water was heated to approximately 60° C. for approximately 2 h. A sample was removed and analyzed by XRPD. The mixture was heated to approximately 70° C. for approximately 17 h. A sample was removed and analyzed by XRPD. The mixture was heated to approximately 80° C. for approximately 7 h. A sample was removed and analyzed by XRPD. The mixture was heated to approximately 90° C. for approximately 13 h. A sample was removed, analyzed by XRPD, and found to be completely hydroxycarbonate polymorph (II). The mixture was allowed to cool to ambient temperature and filtered. The solid was dried under vacuum pump pressure for approximately three days to give 1151 g of hydroxycarbonate polymorph (II).

A portion of the sample was analyzed by XRPD. Another portion was analyzed by an ICP metal scan (Quantitative Technologies Inc.) to give 220 ppm K, and less than 20 ppm for each of the other quantifiable atoms tested. This sample was assayed by titration and Karl Fischer analysis for water content. The sample contained 96.3% lanthanum, 93.6% hydroxy carbonate, and a water content of <1%.

Example 6.2

Preparation of Pure Hydroxycarbonate Polymorph (I)

A mixture of 15.0 g of $La_2O_3$, 24.7 mL of 37.7% hydrochloric acid, and 42 mL of water was cooled to ice bath temperature and filtered. To the cold filtrate was added, dropwise, a solution of 15.7 g of ammonium carbonate in 70 mL of water. The resulting slurry was allowed to warm to ambient temperature and stirred overnight. The solids were recovered by vacuum filtration, washed with three 50-mL portions of water, allowed to dry in the air, and added to a solution of 6.31 g of ammonium carbonate in 107 mL of water. The resulting slurry was heated to reflux for approximately 24 h. A portion of solid was removed, analyzed by XRPD, and found to contain only hydroxycarbonate polymorph (I). The reaction slurry was vacuum filtered and the solids were allowed to dry in the air, washed with 76 mL of water, recovered by vacuum filtration, and again allowed to dry in the air to give 17.7 g of hydroxycarbonate polymorph (I).

A portion of the sample was analyzed by XRPD. Another portion was analyzed by an ICP metal scan (Quantitative Technologies Inc.) to give 214 ppm K, 192 ppm Si, and less than 20 ppm for each of the other quantifiable atoms tested. A 1.3 g portion of this sample was assayed by titration to give 94.6% lanthanum, 94.0% hydroxy carbonate.

Example 6.3

XRD Using Visual and PLS Models

Lanthanum hydroxycarbonate was first analyzed using a visual and partial least squares method using the XRD data. The analytical method for lanthanum hydroxycarbonate in lanthanum carbonate was done as a 2-state process: a visual one and a quantitative one. Stage 1 was the visual evaluation of the XRD spectra to determine if any LHC was visible. The visual technique was used because this gave the lowest limit of detection (LOD) possible, certainly lower than a typical calculation modeling method such as PLS. However PLS modeling and analysis was used for the second stage to provide quantitation of the impurities. This gives LOD and limit of quantitation (LOQ) as follows:

Lanthanum hydroxycarbonate polymorph (I): LOD 1.7% visual LOQ 2% PLS

Lanthanum hydroxycarbonate polymorph (II): LOD 0.3% visual LOQ 3.4% PLS

Similarly, tablet samples were prepared and the LOD for each polymorph was estimated at 0.5% w/w of tablet weight (actually 0.39 and 0.57% for polymorph (I) and (II) respectively). At 0.5% of tablet weight, this equates to 9 mg each of lanthanum hydroxycarbonate polymorph (I) and (II) in an 1800 mg tablet containing 477 mg of lanthanum carbonate tetrahydrate=i.e. around 2% for each polymorph when expressed as lanthanum hydroxycarbonate % w/w of ingoing lanthanum carbonate tetrahydrate).

Lanthanum carbonate quantitative XRD results of the tablets by PLS modeling was not able to detect $LA(CO_3)OH$ polymorph-I (<1.7% w/w), and detected polymorph (II) in the 4 tablets at <3.4%, 13.8%, 20.2%, and <3.4% (w/w).

Example 6.4

XRD Using Rietveld Analysis

X-ray powder diffraction (XRPD) was used to determine the lanthanum hydroxycarbonate (I and II) concentrations in lanthanum carbonate tetrahydrate. Quantitation was based on Rietveld modeling and calibration against a set of 28 standards. Analytical figures-of-merit (accuracy, precision, robustness) were derived from an independent data set. Reported concentrations are weight percent relative to the total drug substance. This method assumes that lanthanum carbonate tetrahydrate was the major component of the active pharmaceutical ingredient, and that the only other species present in the lanthanum carbonate were lanthanum carbonate octahydrate and hydroxycarbonate (I and II).

A. Materials

The materials used to generate calibration and validation samples were sieved using a 106 μm sieve. The hydrates of $La_2(CO_3)_3$ were prepared using methods known in the art such as those described in U.S. Pat. No. 5,968,976. The pure hydroxycarbonate compounds used to make the calibration and validation examples are made in Examples 6.1 and 6.2. All sample mixtures were prepared by geometric mixing to ensure sample homogeneity. The X-ray structure of these samples are shown in FIGS. 1-4. Twenty-eight samples as shown below were made containing two or more of $La_2(CO_3)_3$ tetrahydrate, $La_2(CO_3)_3$ octahydrate, $La(CO_3)OH$ polymorph (I) and $La(CO_3)OH$ polymorph (II).

| Sample | Corrected % tetrahydrate | % octahydrate | % HC(I) | corrected % HC (II) |
|---|---|---|---|---|
| 1 | 93.648 | 2.622 | 2.535 | 1.195 |
| 2 | 93.640 | 2.548 | 0 | 3.812 |
| 3 | 93.801 | 0 | 5.0023 | 1.197 |
| 4 | 93.785 | 5.0185 | 0 | 1.197 |
| 5 | 93.750 | 0 | 2.494 | 3.756 |
| 6 | 93.649 | 1.738 | 1.741 | 2.872 |
| 7 | 93.601 | 0 | 0 | 6.391 |
| 8 | 89.311 | 4.714 | 0 | 5.975 |
| 9 | 88.915 | 9.9502 | 0 | 1.135 |
| 10 | 88.861 | 0 | 4.836 | 6.303 |
| 11 | 88.813 | 0 | 10.054 | 1.133 |
| 12 | 88.777 | 5.054 | 5.036 | 1.133 |
| 13 | 88.686 | 0 | 0 | 11.314 |
| 14 | 87.987 | 3.51 | 3.68 | 4.823 |
| 15 | 79.247 | 0 | 9.859 | 10.894 |
| 16 | 79.105 | 9.910 | 9.976 | 1.009 |
| 17 | 79.042 | 0 | 0 | 20.958 |
| 18 | 78.913 | 0 | 20.08 | 1.007 |
| 19 | 78.706 | 20.29 | 0 | 1.004 |
| 20 | 78.573 | 6.655 | 6.955 | 7.817 |
| 21 | 78.469 | 10.32 | 0 | 11.211 |
| 22 | 69.473 | 14.70 | 14.94 | 0.887 |
| 23 | 69.181 | 0 | 29.936 | 0.883 |
| 24 | 69.079 | 14.90 | 0 | 16.021 |
| 25 | 69.059 | 0 | 15.09 | 15.851 |
| 26 | 68.992 | 0 | 0 | 31.008 |
| 27 | 68.964 | 30.156 | 0 | 0.880 |
| 28 | 67.831 | 9.743 | 10.42 | 12.006 |

B. X-Ray Powder Diffraction Analysis

XRPD analyses were performed using a Shimadzu XRD-6000 X-ray powder diffractometer using Cu Kα radiation. The instrument was equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 1°/min (1.2 sec/0.02° step) from 9 to 40° 2θ was used, and the sample was rotated at 50 rpm during analysis. A silicon standard was analyzed to check the instrument alignment. Data were collected and analyzed using XRD-6000 v. 4.1. Samples were analyzed in a back-fill aluminum holder.

Three individual diffractograms were collected for each sample. Samples were either mixed and repacked into the sample holders between each of the individual runs, or separate aliquots were subsampled from the bulk. The experimental parameters were: continuous scan, 9-40° 2θ, 1°/min scan, 0.02° step, rotate at 50 rpm divergence slit=scatter slit=to, receiving slit=0.15 mm. After obtaining the spectra, the files were converted to ascii-format and the individual diffractograms were x-axis shifted as necessary using the −18.40 reflection of lanthanum carbonate XRPD pattern as the shift GRAMS) and export the files to the format used for the full-pattern analysis (pm format for the Maud Rietveld Analysis software).

C. Data Analysis

XRPD diffractograms were converted to ASCII format using Shimadzu software (Shimadzu XRD-6000 v4.1) or File-Monkey (v1.1), and converted to .spc file format using GRAMS software (v6.0). The diffractograms were examined for two-theta correspondence versus a standard pattern and if necessary, the patterns were x-axis shifted using the −18.4° reflection as the shift reference. The diffractograms were then converted to prn format using GRAMS, and Rietveld analysis was performed using Maud software (Material Analysis Using Diffraction; www.ing.unitn.it/luttero/maud/, v1.998).

Rietveld results from the triplicate determinations of each sample were averaged, and calibration equations were developed by regressing the actual analyte content of the standards versus the Rietveld results.

The percent recovery for the validation samples was calculated using the following equation:

% Recovery=(Predicted % Analyze)/(Actual % Analyte)×100%

A pooled standard deviation was calculated from the results of replicate analyses of multiple samples using the following equation:

Pooled standard deviation=$(SStotaUdf)^{1/2}$, where: SStotal=sum of squares of deviations from the mean for all samples df=degrees of freedom (total number of replicates−total number of samples)

D. Specificity

Figure 5:
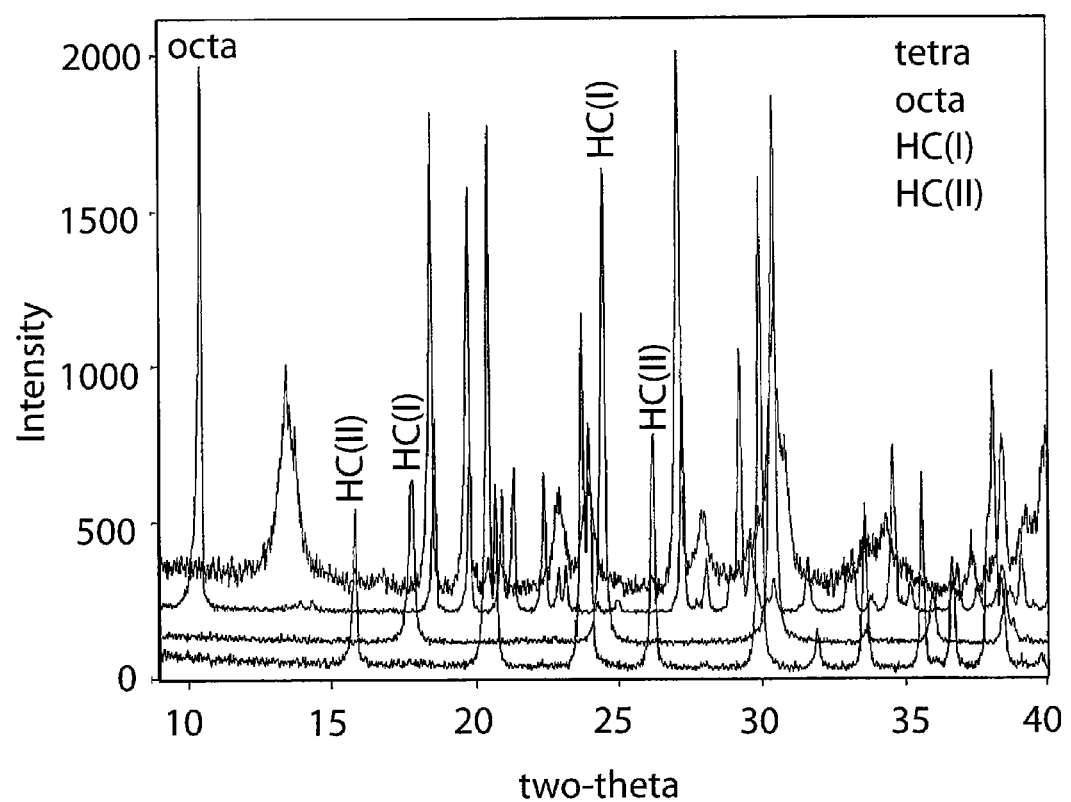
FIG. 5 is an overlay of 4 XRPD patterns of $La_2(CO_3)_3$ $4H_2O$ (top pattern), $La_2(CO_3)_3 \cdot 8H_2O$, $La(CO_3)OH_3$ form (I) and $La(CO_3)OH$ form (II) (bottom pattern).
Figure 6:
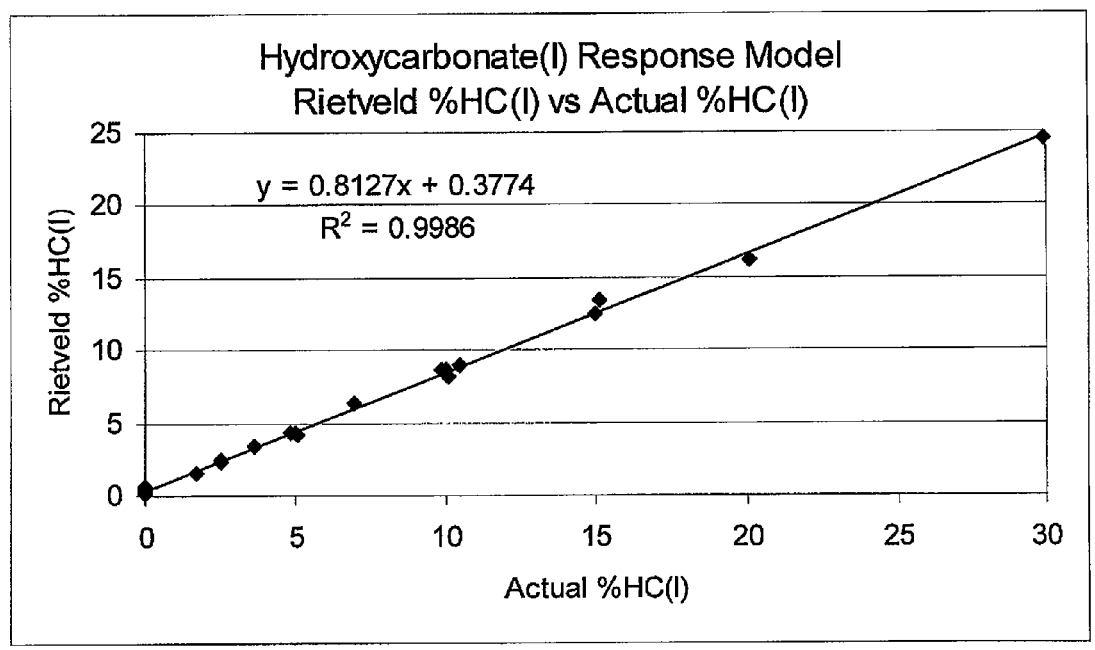
FIG. 6 depicts the actual concentration of $La(CO_3)OH$ form (I) standards compared to the concentration of $La(CO_3)OH$ form (I) as calculated by the Rietveld method and a linear regression.
Figure 7:
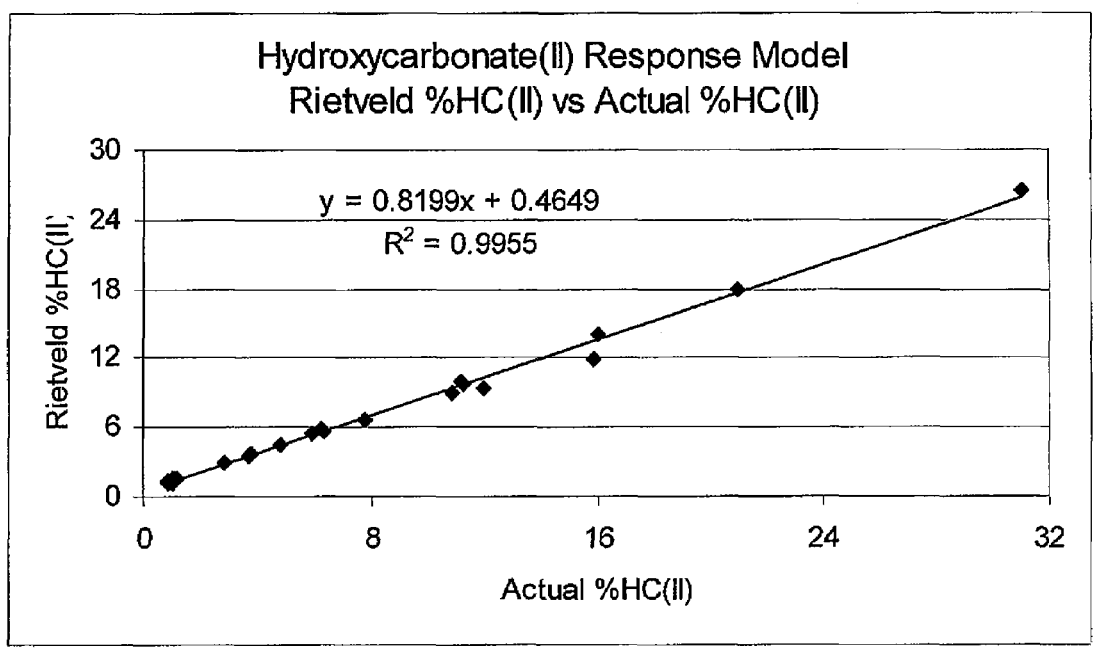
FIG. 7 depicts the actual concentration of $La(CO_3)OH$ form (II) standards compared to the concentration of $La(CO_3)OH$ form (II) as calculated by the Rietveld method and a linear regression.
Figure 8:
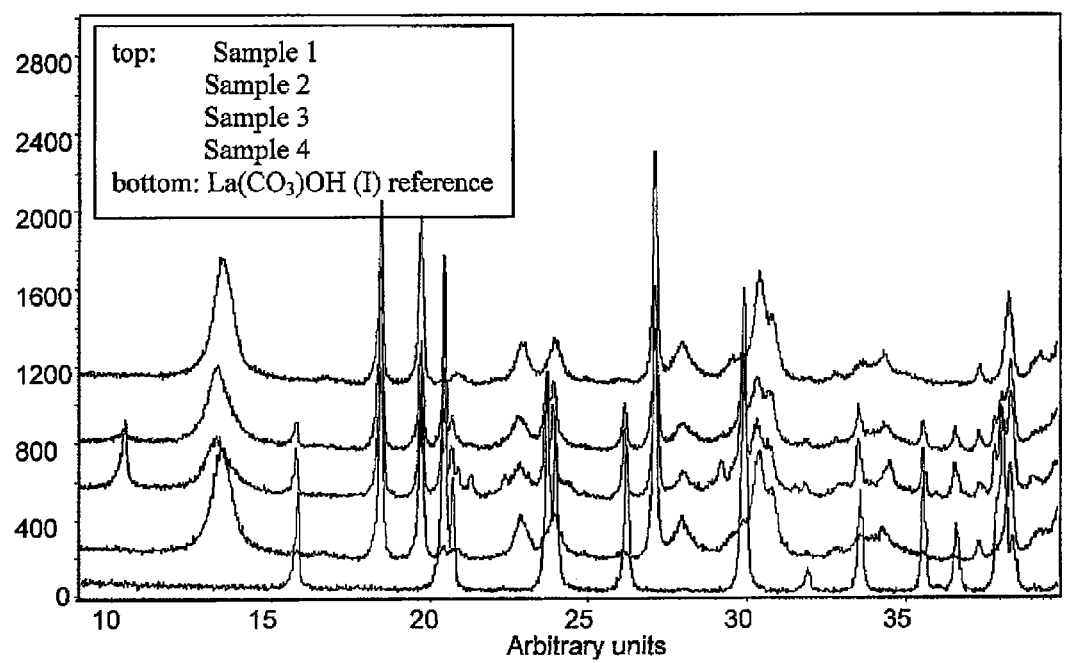
FIG. 8 is an XRD Overlay of four samples containing $La_2(CO_3)_3 \cdot 4H_2O$ and $La(CO_3)OH$ and a $La(CO_3)OH$ standard.
Figure 9:
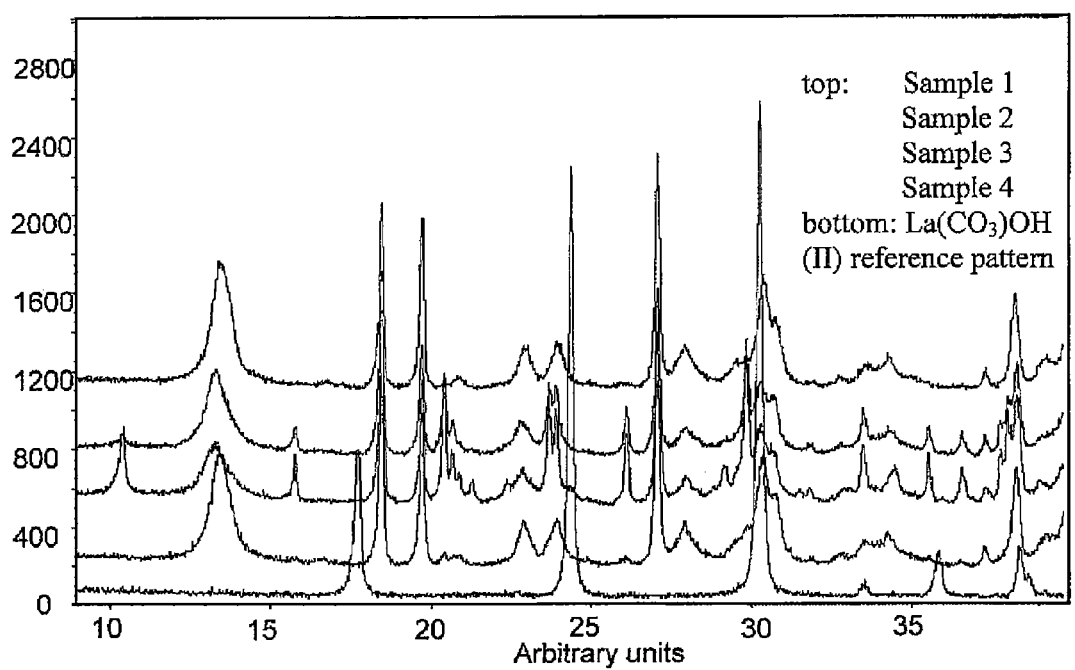
FIG. 9 is an XRD Overlay of four samples containing $La_2(CO_3)_3 \cdot 4H_2O$ and $La(CO_3)OH$ and a $La(CO_3)OH$ standard.

XRPD patterns of the lanthanum carbonate tetrahydrate, octahydrate, and hydroxycarbonate (I), and hydroxycarbonate (II) used as components for calibration and validation mixtures are shown in FIGS. 1-4. Visual examination of the XRPD overlay of the four components (FIG. 5) shows regions in which any single component can be clearly differentiated from the others. XRPD analysis demonstrates specificity for these components and is therefore a suitable technique for quantitation.

E. Linearity and Range

Rietveld results for the 28 mixtures used as calibration standards and the average values for the triplicate determinations are:

| Sample | Actual % HC(I) | Rietveld Avg % HC(I) | Error | Actual % HC(II) | Rietveld Avg % HC(II) | Error |
|---|---|---|---|---|---|---|
| 1 | 2.54 | 2.36 | 0.03 | 1.20 | 1.58 | 0.15 |
| 2 | 0.00 | 0.52 | 0.27 | 3.81 | 3.64 | 0.03 |
| 3 | 5.00 | 4.35 | 0.43 | 1.20 | 1.54 | 0.12 |
| 4 | 0.00 | 0.35 | 0.12 | 1.20 | 1.54 | 0.12 |
| 5 | 2.49 | 2.40 | 0.01 | 3.76 | 3.59 | 0.03 |
| 6 | 1.74 | 1.60 | 0.02 | 2.87 | 2.98 | 0.01 |
| 7 | 0.00 | 0.41 | 0.17 | 6.39 | 5.58 | 0.66 |
| 8 | 0.00 | 0.35 | 0.12 | 5.97 | 5.54 | 0.19 |
| 9 | 0.00 | 0.15 | 0.02 | 1.13 | 1.35 | 0.05 |
| 10 | 4.84 | 4.30 | 0.29 | 6.30 | 5.76 | 0.30 |
| 11 | 10.05 | 8.23 | 3.31 | 1.13 | 1.57 | 0.19 |
| 12 | 5.04 | 4.19 | 0.72 | 1.13 | 1.53 | 0.16 |
| 13 | 0.00 | 0.57 | 0.32 | 11.31 | 9.66 | 2.75 |
| 14 | 3.68 | 3.45 | 0.05 | 4.82 | 4.52 | 0.09 |
| 15 | 9.86 | 8.62 | 1.54 | 10.89 | 8.96 | 3.73 |
| 16 | 9.98 | 8.64 | 1.78 | 1.01 | 1.38 | 0.13 |
| 17 | 0.00 | 0.54 | 0.30 | 20.96 | 17.97 | 8.93 |
| 18 | 20.08 | 16.28 | 14.44 | 1.01 | 1.55 | 0.29 |
| 19 | 0.00 | 0.10 | 0.01 | 1.00 | 1.22 | 0.05 |
| 20 | 6.96 | 6.26 | 0.48 | 7.82 | 6.59 | 1.50 |
| 21 | 0.00 | 0.30 | 0.09 | 11.21 | 9.84 | 1.87 |
| 22 | 14.94 | 12.54 | 5.79 | 0.89 | 1.13 | 0.06 |
| 23 | 29.94 | 24.56 | 28.90 | 0.88 | 1.38 | 0.25 |
| 24 | 0.00 | 0.39 | 0.15 | 16.02 | 14.10 | 3.70 |
| 25 | 15.09 | 13.3 | 2.91 | 15.85 | 11.97 | 15.04 |
| 26 | 0.00 | 0.56 | 0.31 | 31.01 | 26.59 | 19.52 |
| 27 | 0.00 | 0.24 | 0.06 | 0.88 | 1.12 | 0.06 |
| 28 | 10.42 | 8.96 | 2.12 | 12.01 | 9.44 | 6.60 |

The standard error was calculated to be 0.2318 for form (I) and 0.4128 for form (II). Calibration models based on these averages were then determined.

1. Hydroxycarbonate (I) Calibration Model

The Rietveld hydroxycarbonate (I) response was done for the 28 calibration standards spanning 0-30% hydroxycarbonate(I). The root-mean-square error of the uncalibrated Rietveld data is 1.52%. The slope of the response curve is the sensitivity of the Rietveld response per unit concentration (0.8127). This slope is subsequently used in calculating the minimum quantitation limit for hydroxycarbonate (I) determination.

The response data were used to generate a linear regression model for hydroxycarbonate (I) determination across the full calibration range. The predictive equation is:

% Hydroxycarbonate (I)=1.2287×(Rietveld ° HC(I))−0.456

The correlation coefficient for this model is 0.9986, and the predicted values from this model exhibit a root-mean-square error of 0.27%.

2. Hydroxycarbonate(II) Calibration Model

The Rietveld hydroxycarbonate(II) response for the 28 calibration standards spanned a concentration range of 0.9-31% hydroxycarbonate. The root-mean-square error of the uncalibrated Rietveld data is 1.54%. The slope of this curve is the sensitivity of the Rietveld response per unit concentration (0.8199). This slope is subsequently used in calculating the minimum quantitation limit for hydroxycarbonate (II) determination.

The response data were used to generate a linear regression model for hydroxycarbonate (II) determination across the full calibration range. The predictive equation is:

% Hydroxycarbonate (II)=1.2143×(Rietveld % HC(II))−0.5353

The correlation coefficient for this model is 0.9955, and the predicted values from this model exhibit a root-mean-square error of 0.4861%.

F. Precision

Method precision was determined by the analysis of 9 lanthanum carbonate samples that exhibit visually non-detectable response for hydroxycarbonate (I and II) and have varying concentrations of $La_2(CO_3)_3 \cdot 4H_2O$. These were analyzed by the procedure outlined hereinabove. This estimate of precision therefore encompasses uncertainty due to variations in:

(1) Sample matrix (samples represent multiple lots and various storage conditions), (2) Sample presentation (different sample holders and autosampler positions used), and (3) Data analysis (x-axis shifting and subsequent Rietveld analysis).

The Rietveld responses and predicted analyte concentrations for the samples used are used to calculate the 95% confidence intervals for the experimental results. The standard deviations and 95% confidence intervals for hydroxycarbonate (I and II) determination are summarized below:

|  | Hydroxycarbonate (I) | Hydroxycarbonate (II) |
| --- | --- | --- |
| Average | −0.13% | 0.02% |
| Standard Deviation, σ | 0.229% | 0.091% |
| 95% Confidence Interval | 0.46% | 0.18% |

G. Detection Limit

The detection limit (LOD) was established by calculating the upper 99% confidence limit of the response observed in the 9 samples visually free of analyte. These values are:

| Analyte | Average Predicted Concentration (Analyte-free Samples) | Standard Deviation | Detection Limit |
| --- | --- | --- | --- |
| HC(I) | −0.13% | 0.229% | 0.55% |
| HC(II) | 0.02% | 0.091% | 0.29% |

H. Minimum Quantitation Limit

The minimum quantitation limit (MQL), expressed as 10(σ/S), where σ is the standard deviation of the response observed in the 9 samples visually free of analyte and S is the slope, i.e., the Rietveld response over the true analyte content. Results are summarized below.

| Analyte | Standard Deviation | Slope | Minimum Quantitation Limit |
| --- | --- | --- | --- |
| HC (I) | 0.229 | 0.8127 | 2.82% |
| HC (II) | 0.091 | 0.8199 | 1.11% |

I. Accuracy of the Validation Standards

Accuracy may be reported as percent recovery by the assay of the known amount of analyte in the validation standard. Six validation standards were prepared, with analyte concentrations ranging from 0.5 to 10% for HC(I) and 1.8 to 10.9% for HC(II). Octahydrate was allowed to vary from 0.5 to 10%.

Recovery data for the validation standards for hydroxycarbonate (I) and (II), respectively are:

| Accuracy of Validation Standards | | |
| --- | --- | --- |
| Analyte | Actual Range, % | % Recovery (all data) |
| HC (I) | 4.3–10.1 | 90.4 + 9.0 |
| HC (II) | 1.8–10.9 | 98.1 ± 6.4 |

J. System Suitability

To evaluate system suitability, results obtained when the XRPD tube intensity was significantly lowered were examined for accuracy. Lower intensities were achieved experimentally by lowering the accelerating voltage from 40 kV to 20 kV. This resulted in a 74% reduction in tube intensity. This sample was reliably predicted under these conditions (the average Rietveld % of HC(I) changed from 1.67% to 1.70% and the average Rietveld % of HC(II) changed from 3.13% to 3.17%). This therefore demonstrates system suitability.

K. Ruggedness

Two samples were analyzed by two different analysts, and one sample was further analyzed on two different instruments. No bias between the operators or instrument was observed. The results of % HC(I) and % HC(II) determinations are:

| Sample | Analyst | Instrument | Predicted % HC (I) | Predicted % HC (II) |
| --- | --- | --- | --- | --- |
| 1 | A | X | 1.67 | 3.36 |
| 1 | A | X | 1.51 | 3.31 |
| 1 | B | X | 1.61 | 3.39 |
| 1 | B | X | 1.59 | 3.27 |
| 2 | A | X | 9.87 | 11.27 |
| 2 | A | X | 9.81 | 9.68 |
| 2 | B | X | 10.15 | 10.89 |
| 2 | B | X | 10.03 | 10.25 |
| 2 | B | X | 9.46 | 9.26 |
| 2 | B | Y | 10.10 | 10.29 |
| 2 | B | Y | 10.03 | 10.31 |

L. Conclusion

This quantitative method is applicable for the determination of lanthanum hydroxycarbonate (I and II) in lanthanum carbonate tetrahydrate lanthanum carbonate samples. The method is preferred for samples containing at least 68% of $La_2(CO_3)_3$ tetrahydrate. XRPD analysis can reliably determine lanthanum hydroxycarbonate (I and II) in lanthanum carbonate lanthanum carbonate as summarized below:

| Analyte | Detection Limit (LOD) | Quantitation Limit (MQL) | Upper Analytical Limit |
| --- | --- | --- | --- |
| Hydroxycarbonate (I) | 0.55% | 2.82% | 30% |
| Hydroxycarbonate (II) | 0.29% | 1.11% | 31% |

Example 6.4

XRD of Tablets Using Rietveld Analysis

This technique has been validated for lanthanum carbonate tablets as well as powders. The tablets can be represented as % weight of LHC/weight of ingoing lanthanum carbonate hydrate. Lanthanum hydroxycarbonate polymorph (I) and (II) limit of detection (LOD) and LOQ for the tablet by Rietveld analysis is provided as follows, with the number in parentheses corresponding to the equivalent percent of ingoing lanthanum carbonate hydrate.

| Analyte | Detection Limit (LOD) | Quantitation Limit (MQL) |
| --- | --- | --- |
| Hydroxycarbonate (I) | 0.65% (2.5%) | 1.8% (6.8%) |
| Hydroxycarbonate (II) | 0.23% (0.9%) | 2.0% (7.6%) |

The present invention is not to be limited in scope by the specific embodiments described herein. Indeed, various modifications of the invention in addition to those described herein will be apparent to those skilled in the art from the foregoing description. Such modifications are intended to fall within the scope of the appended claims.

All references cited herein, including all patents, published patent applications, and published scientific articles and books, are incorporated by reference in their entireties for all purposes.

What is claimed is:

1. A method of treating hyperphosphatemia in a subject comprising:
   (i) obtaining a crude lanthanum carbonate composition comprising lanthanum carbonate having the formula $La_2(CO_3)_3 \cdot xH_2O$ wherein x has a value from 3 to 6 and lanthanum hydroxy carbonate;
   (ii) subjecting the crude lanthanum carbonate to a purity assay comprising the steps:
      (a) obtaining an X-ray diffraction pattern of the crude lanthanum carbonate composition;
      (b) obtaining a plurality of reference samples containing the lanthanum hydroxy carbonate;
      (c) obtaining a plurality of X-ray diffraction patterns of the reference samples; and
      (d) performing Rietveld analysis on the X-ray diffraction patterns to obtain:
         the detection limit, minimum quantitation limit (MQL), and/or upper analytical limit from the reference samples and
         the predicted impurity concentration value from the crude lanthanum carbonate composition pattern, and
   (iii) when the lanthanum carbonate composition contains no more than 0.55% lanthanum hydroxycarbonate form (I) or no more than 0.29% lanthanum hydroxycarbonate form (II) according to the assay of (ii), administering to said subject an amount of the lanthanum carbonate composition effective to treat said hyperphosphatemia.

2. The method of claim 1, wherein x has a value from 3.5 to 5.

3. The method of claim 1, wherein x has a value from 3.8 to 4.5.

4. The method of claim 3, wherein said administering is by an oral route.

5. The method of claim 1, wherein the impurity comprises lanthanum hydroxycarbonate ($La(CO_3)OH$).

6. The method of claim 5, wherein the impurity comprises a combination of $La(CO_3)OH$ form (I) and form (II).

7. The method of claim 5, wherein the lanthanum hydroxycarbonate (I) is characterized by an X-ray powder diffraction pattern having peaks at approximately 17.7°, 24.4°, and 30.3° two theta.

8. The method of claim 6, wherein the amount of lanthanum hydroxycarbonate administered in step (iii) is up to 0.55% lanthanum hydroxycarbonate form (I) and up to 0.29% lanthanum hydroxycarbonate form (II).

9. The method of claim 1, wherein the lanthanum carbonate composition administered in step (iii) comprises at least 68% $La_2(CO_3)_3 \cdot 4H_2O$.

10. The method of claim 1, wherein the lanthanum carbonate composition administered in step (iii) is at least 95% pure lanthanum carbonate.

11. The method of claim 8, wherein the lanthanum carbonate composition administered in step (iii) is at least 99% pure lanthanum carbonate.

12. A method of treating hyperphosphatemia in a subject comprising:
   (i) obtaining a lanthanum carbonate composition comprising lanthanum carbonate having the formula $La_2(CO_3)_3 \cdot xH_2O$ wherein x has a value from 3 to 6, and at least one lanthanum hydroxycarbonate impurity;
   (ii) applying a purity assay to identify substantially pure lanthanum carbonate containing no more than 0.55% lanthanum hydroxycarbonate form (I) or no more than 0.29% lanthanum hydroxycarbonate form (II), wherein the purity assay comprises the steps of:
      (a) obtaining an X-ray diffraction pattern of the lanthanum carbonate composition;
      (b) obtaining a plurality of reference samples containing the lanthanum hydroxy carbonate;
      (c) obtaining a plurality of X-ray diffraction patterns of the reference samples; and
      (d) performing Rietveld analysis on the X-ray diffraction patterns to obtain:
         the detection limit, minimum quantitation limit (MQL), and/or upper analytical limit from the reference samples and
         the predicted lanthanum hydroxycarbonate concentration value from the lanthanum carbonate composition pattern; and
   (iii) administering to said subject the substantially pure lanthanum carbonate compositions containing no more than 0.55% lanthanum hydroxycarbonate form (I) or no more than 0.29% lanthanum hydroxycarbonate form (II), in an amount effective to treat said hyperphosphatemia.

13. The method of claim 12 wherein x has a value from 3.5 to 5.

14. The method of claim 13 wherein x has a value from 3.8 to 4.5.

15. The method of claim 12, wherein said administering is by an oral route.

16. The method of claim 12, wherein the lanthanum carbonate composition administered in step (iii) comprising 0.55% or less lanthanum hydroxycarbonate (I) and 0.29% or less lanthanum hydroxycarbonate form (II).

17. The method of claim 16, wherein the lanthanum hydroxycarbonate (I) is characterized by an X-ray powder diffraction pattern having peaks at approximately 17.7°, 24.4°, and 30.3° two theta.

18. The method of claim 12, wherein the lanthanum carbonate composition administered in step (iii) is at least 95% pure lanthanum carbonate.

19. A method of treating hyperphosphatemia in a subject comprising:
   (i) obtaining a crude lanthanum carbonate composition;
   (ii) measuring the purity of the lanthanum carbonate composition, wherein the measuring comprises:
      (a) obtaining an X-ray diffraction pattern of the crude lanthanum carbonate composition;
      (b) obtaining a plurality of reference samples containing lanthanum hydroxy carbonate;
      (c) obtaining a plurality of X-ray diffraction patterns of the reference samples; and
      (d) performing Rietveld analysis on the X-ray diffraction patterns to obtain the predicted lanthanum hydroxy carbonate concentration value from the crude lanthanum carbonate composition pattern,
   (iii) administering to said subject an amount of the lanthanum carbonate composition in the form of a tablet containing 0.65% or less lanthanum hydroxycarbonate (I) and 0.23% or less lanthanum hydroxycarbonate (II) as predicted by step (ii) wherein said lanthanum carbonate composition is effective to treat said hyperphosphatemia.

* * * * *